United States Patent
Saito et al.

(10) Patent No.: US 12,237,346 B2
(45) Date of Patent: Feb. 25, 2025

(54) DETECTION DEVICE WITH STACKED PHOTODIODES

(71) Applicants: Japan Display Inc., Tokyo (JP); The University of Tokyo, Tokyo (JP)

(72) Inventors: Keiichi Saito, Tokyo (JP); Takashi Nakamura, Tokyo (JP); Gen Koide, Tokyo (JP); Takao Someya, Tokyo (JP); Tomoyuki Yokota, Tokyo (JP)

(73) Assignees: Japan Display Inc., Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 18/225,809

(22) Filed: Jul. 25, 2023

(65) Prior Publication Data

US 2023/0369355 A1    Nov. 16, 2023

Related U.S. Application Data

(63) Continuation of application No. PCT/JP2022/002773, filed on Jan. 26, 2022.

(30) Foreign Application Priority Data

Jan. 26, 2021  (JP) .................................. 2021-010589

(51) Int. Cl.
   *H01L 27/144* (2006.01)
   *H01L 31/101* (2006.01)
(52) U.S. Cl.
   CPC ...... *H01L 27/1446* (2013.01); *H01L 31/1013* (2013.01)
(58) Field of Classification Search
   CPC ............. H01L 27/1446; H01L 31/1013; H01L 27/146; H01L 27/14647; H01L 31/10; A61B 5/1171; A61B 5/1172; A61B 5/1455; H04N 25/70; H10K 39/00
   USPC ........................................................ 250/208.1
   See application file for complete search history.

(56) References Cited

U.S. PATENT DOCUMENTS

| | | | |
|---|---|---|---|
| 10,732,303 B2 * | 8/2020 | Moriwaki | H01L 27/14663 |
| 2009/0027358 A1 | 1/2009 | Hosono | |
| 2015/0129747 A1 * | 5/2015 | Petilli | H01L 27/14627 257/432 |
| 2017/0179198 A1 * | 6/2017 | Li | H10K 39/12 |
| 2018/0019269 A1 * | 1/2018 | Klipstein | H01L 31/101 |
| 2018/0204890 A1 | 7/2018 | Akimoto | |

(Continued)

FOREIGN PATENT DOCUMENTS

| | | |
|---|---|---|
| DE | 102011081564 A1 | 2/2013 |
| JP | 2009032005 A | 2/2009 |
| JP | 2018116108 A | 7/2018 |

OTHER PUBLICATIONS

International Search Report of corresponding PCT application PCT/JP2022/002773, dated Apr. 12, 2022.

(Continued)

*Primary Examiner* — Thanh Luu
*Assistant Examiner* — Mai Thi Ngoc Tran
(74) *Attorney, Agent, or Firm* — K&L Gates LLP

(57) ABSTRACT

According to an aspect, a detection device includes a plurality of optical sensors arranged on a substrate. Each of the optical sensors includes a first photodiode and a second photodiode that is coupled in series and in an opposite direction to the first photodiode.

7 Claims, 10 Drawing Sheets

(56) References Cited

U.S. PATENT DOCUMENTS

2023/0225149 A1* 7/2023 Watabe ................ H10K 85/631
257/40

OTHER PUBLICATIONS

Office Action issued in related Japanese Patent Application No. 2022-578436, issued on Apr. 23, 2024 and English translation of same. 8 pages.

* cited by examiner

DETECTION DEVICE WITH STACKED PHOTODIODES

CROSS-REFERENCE TO RELATED APPLICATION

This application claims the benefit of priority from Japanese Patent Application No. 2021-010589 filed on Jan. 26, 2021 and International Patent Application No. PCT/JP2022/002773 filed on Jan. 26, 2022, the entire contents of which are incorporated herein by reference.

BACKGROUND

1. Technical Field

What is disclosed herein relates to a detection device.

2. Description of the Related Art

Optical sensors capable of detecting fingerprint patterns and vascular patterns are known (for example, Japanese Patent Application Laid-open Publication No. 2009-032005). Among such optical sensors, flexible sheet sensors are known each using an organic semiconductor material as an active layer.

In the optical sensors, a reverse bias voltage is supplied during detection, which may cause a change in sensitivity characteristics over time.

For the foregoing reasons, there is a need for a detection device capable of reducing the change in the sensitivity characteristics.

SUMMARY

According to an aspect, a detection device includes a plurality of optical sensors arranged on a substrate. Each of the optical sensors includes a first photodiode and a second photodiode that is coupled in series and in an opposite direction to the first photodiode.

DETAILED DESCRIPTION

Figure 1:
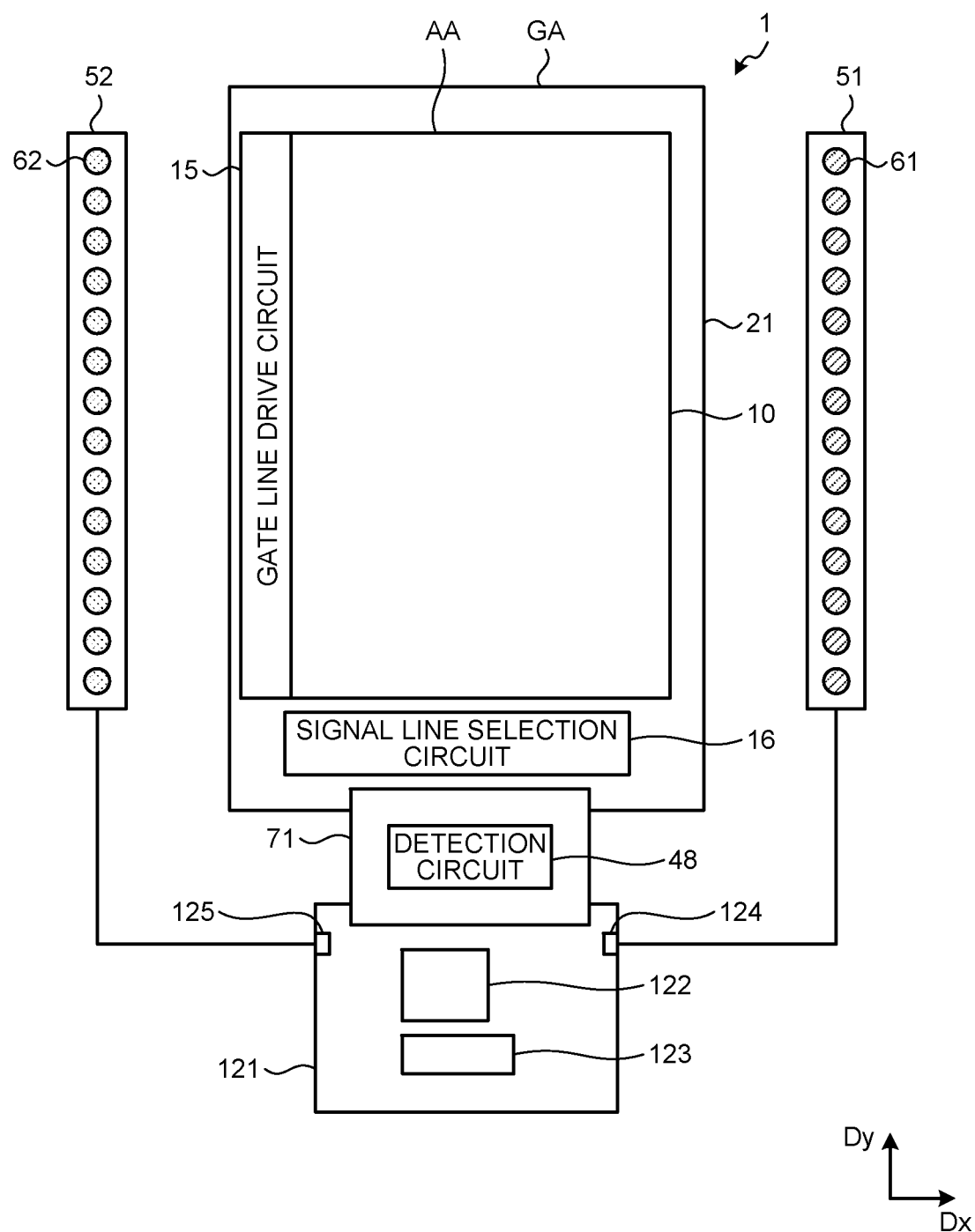
FIG. 1 is a plan view illustrating a detection device according to a first embodiment.

The following describes modes (embodiments) for carrying out the present disclosure in detail with reference to the drawings. The present disclosure is not limited to the description of the embodiments given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In the present specification and claims, in expressing an aspect of disposing another structure on or above a certain structure, a case of simply expressing "on" includes both a case of disposing the other structure immediately on the certain structure so as to contact the certain structure and a case of disposing the other structure above the certain structure with still another structure interposed therebetween, unless otherwise specified.

First Embodiment

FIG. 1 is a plan view illustrating a detection device according to a first embodiment. As illustrated in FIG. 1, a detection device 1 includes a sensor base member 21, a sensor 10, a gate line drive circuit 15, a signal line selection circuit 16, a detection circuit 48, a control circuit 122, a power supply circuit 123, a first light source base member 51, a second light source base member 52, a first light source 61, and a second light source 62. The first light source base member 51 is provided with a plurality of the first light sources 61. The second light source base member 52 is provided with a plurality of the second light sources 62.

The sensor base member 21 is electrically coupled to a control substrate 121 through a flexible printed circuit board 71. The flexible printed circuit board 71 is provided with the detection circuit 48. The control substrate 121 is provided with the control circuit 122 and the power supply circuit 123. The control circuit 122 is, for example, a field-programmable gate array (FPGA). The control circuit 122 supplies control signals to the sensor 10, the gate line drive circuit 15, and the signal line selection circuit 16 to control a detection operation of the sensor 10. The control circuit 122 also supplies control signals to the first and the second light sources 61 and 62 to control lighting and non-lighting of the first and the second light sources 61 and 62. The power supply circuit 123 supplies voltage signals including, for example, a drive signal (drive voltage) VDDSNS (refer to FIG. 4) to the sensor 10, the gate line drive circuit 15, and the signal line selection circuit 16. The power supply circuit 123 also supplies a power supply voltage to the first and the second light sources 61 and 62.

The sensor base member 21 has a detection area AA and a peripheral area GA. The detection area AA is an area provided with a plurality of optical sensors PD (refer to FIG. 4) included in the sensor 10. The peripheral area GA is an area between the outer perimeter of the detection area AA and the ends of the sensor base member 21, and is an area not provided with the optical sensors PD.

The gate line drive circuit 15 and the signal line selection circuit 16 are provided in the peripheral area GA. Specifically, the gate line drive circuit 15 is provided in an area extending along a second direction Dy in the peripheral area GA. The signal line selection circuit 16 is provided in an area extending along a first direction Dx in the peripheral area GA, and is provided between the sensor 10 and the detection circuit 48.

The first direction Dx is one direction in a plane parallel to the sensor base member 21. The second direction Dy is one direction in the plane parallel to the sensor base member 21, and is a direction orthogonal to the first direction Dx. The second direction Dy may non-orthogonally intersect the first direction Dx.

The first light sources 61 are provided on the first light source base member 51, and are arranged along the second direction Dy. The second light sources 62 are provided on the second light source base member 52, and are arranged along the second direction Dy. The first light source base member 51 and the second light source base member 52 are electrically coupled, through respective terminals 124 and 125, provided on the control substrate 121, to the control circuit 122 and the power supply circuit 123.

For example, inorganic light-emitting diodes (LEDs) or organic electroluminescent (EL) diodes (organic light-emitting diodes (OLEDs)) are used as the first and the second light sources 61 and 62. The first and the second light sources 61 and 62 emit first light and second light, respectively, having different wavelengths.

The first light emitted from the first light sources 61 is mainly reflected on a surface of an object to be detected, such as a finger Fg, and is incident on the sensor 10. As a result, the sensor 10 can detect a fingerprint by detecting a shape of asperities on the surface of the finger Fg or the like. The second light emitted from the second light sources 62 is mainly reflected in the finger Fg or the like, or transmitted through the finger Fg or the like, and is incident on the sensor 10. As a result, the sensor 10 can detect information on a living body in the finger Fg or the like. Examples of the information on the living body include pulse waves, pulsation, and a vascular image of the finger Fg or a palm. That is, the detection device 1 may be configured as a fingerprint detection device to detect a fingerprint or a vein detection device to detect a vascular pattern of, for example, veins.

The first light may have a wavelength of from 500 nm to 600 nm, for example, a wavelength of approximately 550 nm, and the second light may have a wavelength of from 780 nm and 950 nm, for example, a wavelength of approximately 850 nm. In this case, the first light is blue or green visible light, and the second light is infrared light. The sensor 10 can detect the fingerprint based on the first light emitted from the first light sources 61. The second light emitted from the second light sources 62 is reflected in the object to be detected such as the finger Fg, or transmitted through or absorbed by the finger Fg or the like, and is incident on the sensor 10. As a result, the sensor 10 can detect the pulse waves or the vascular image (vascular pattern) as the information on the living body in the finger Fg or the like.

Alternatively, the first light may have a wavelength of from 600 nm to 700 nm, for example, approximately 660 nm, and the second light may have a wavelength of from 780 nm to 900 nm, for example, approximately 850 nm. In this case, the sensor 10 can detect a blood oxygen saturation level in addition to the pulse waves, the pulsation, and the vascular image as the information on the living body based on the first light emitted from the first light sources 61 and the second light emitted from the second light sources 62. Thus, the detection device 1 includes the first and the second light sources 61 and 62, and therefore, can detect the various information on the living body by performing the detection based on the first light and the detection based on the second light.

The arrangement of the first and the second light sources 61 and 62 illustrated in FIG. 1 is merely an example, and may be changed as appropriate. The detection device 1 is provided with a plurality of types of light sources (first and second light sources 61 and 62) as the light sources. However, the light sources are not limited thereto, and may be of one type. For example, the first and the second light sources 61 and 62 may be arranged on each of the first and the second light source base members 51 and 52. The first and the second light sources 61 and 62 may be provided on one light source base member, or three or more light source base members. Alternatively, only at least one light source needs to be disposed. However, the light sources are not limited to the above description, but may be light sources of one type that emit light ranging over different wavelength ranges in which the detection device 1 has (a first photodiode PDa and a second photodiode PDb (refer to FIG. 4) have) detection sensitivity.

Figure 2:
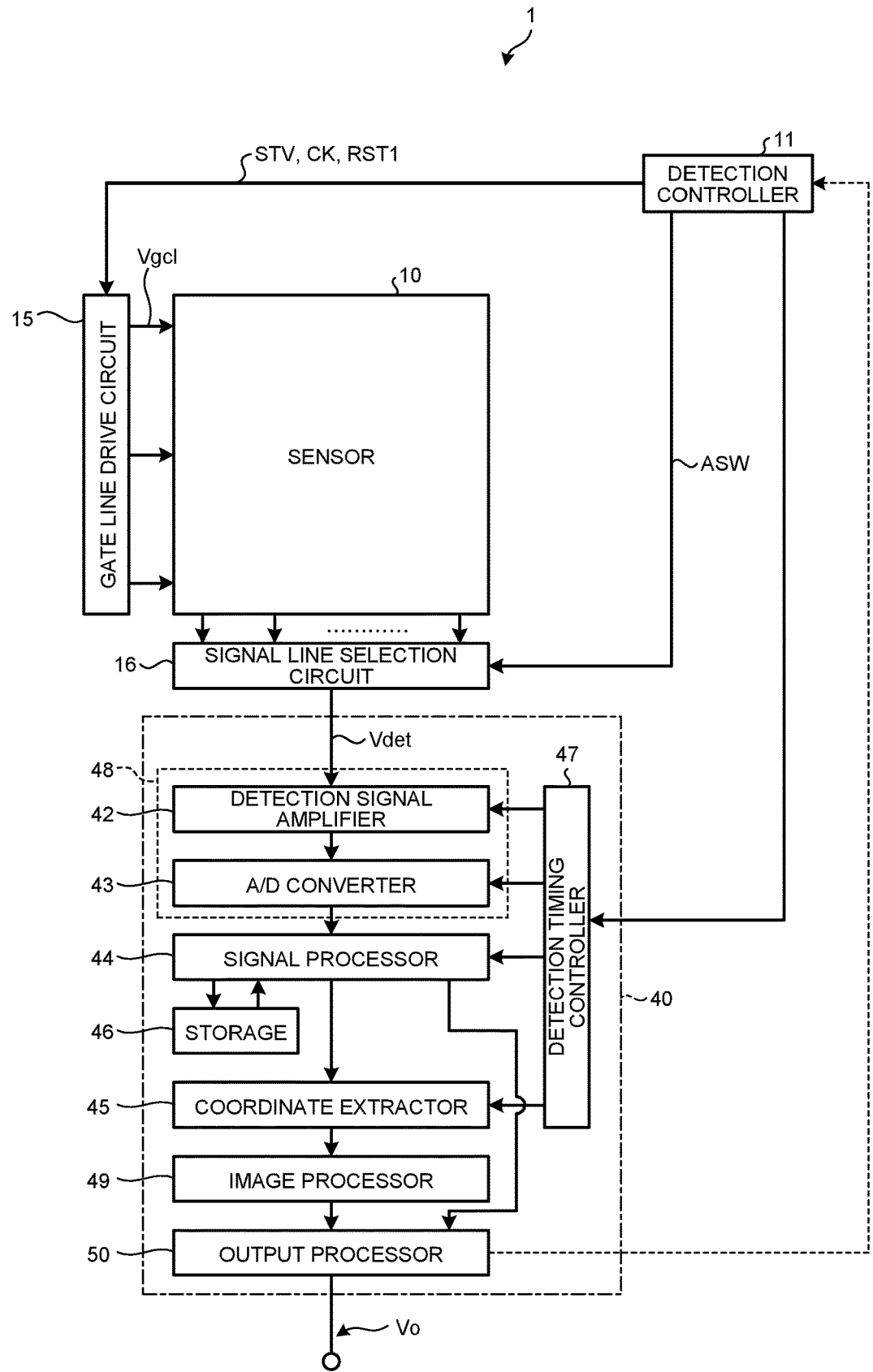
FIG. 2 is a block diagram illustrating a configuration example of the detection device according to the first embodiment.

FIG. 2 is a block diagram illustrating a configuration example of the detection device according to the first embodiment. As illustrated in FIG. 2, the detection device 1 further includes a detection controller (detection control circuit) 11 and a detector (detection signal processing circuit) 40. The control circuit 122 includes one, some, or all functions of the detection controller 11. The control circuit 122 also includes one, some, or all functions of the detector 40 other than those of the detection circuit 48.

The sensor 10 includes the optical sensors PD. Each of the optical sensors PD included in the sensor 10 is a photodiode, and outputs an electrical signal corresponding to light emitted thereto as a detection signal Vdet to the signal line selection circuit 16. The sensor 10 performs the detection according to a gate drive signal Vgcl supplied from the gate line drive circuit 15.

The detection controller 11 is a circuit that supplies respective control signals to the gate line drive circuit 15, the signal line selection circuit 16, and the detector 40 to control operations of these components. The detection controller 11 supplies various control signals including, for example, a start signal STV, a clock signal CK, and a reset signal RST1 to the gate line drive circuit 15. The detection controller 11 also supplies various control signals including, for example, a selection signal ASW to the signal line selection circuit 16. The detection controller 11 also supplies various control signals to the first and the second light sources 61 and 62 to control the lighting and the non-lighting of each group of the first and the second light sources 61 and 62.

The gate line drive circuit 15 is a circuit that drives a plurality of gate lines GCL (refer to FIG. 3) based on the various control signals. The gate line drive circuit 15 sequentially or simultaneously selects the gate lines GCL, and supplies the gate drive signals Vgcl to the selected gate lines GCL. By this operation, the gate line drive circuit 15 selects the optical sensors PD electrically coupled to the gate lines GCL.

Figure 3:
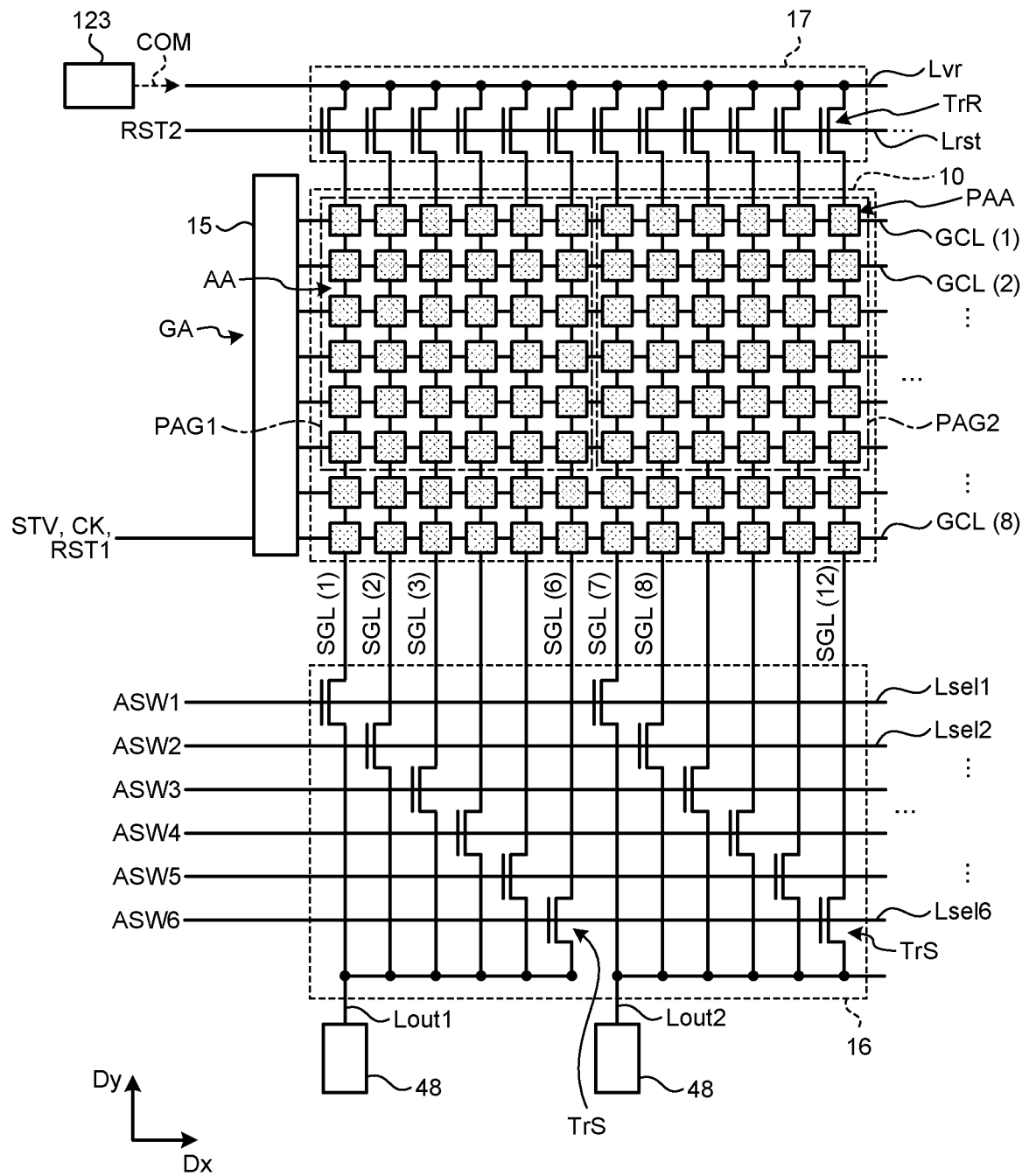
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 is, for example, a multiplexer. The signal line selection circuit 16 electrically couples the selected signal lines SGL to the detection circuit 48 based on the selection signal ASW supplied from the detection controller 11. By this operation, the signal line selection circuit 16 outputs the detection signal Vdet of the optical sensor PD to the detector 40.

The detector 40 includes the detection circuit 48, a signal processor (signal processing circuit) 44, a coordinate extractor (coordinate extraction circuit) 45, a storage (storage circuit) 46, a detection timing controller (detection timing control circuit) 47, an image processor (image processing circuit) 49, and an output processor (output processing circuit) 50. Based on a control signal supplied from the detection controller 11, the detection timing controller 47 controls the detection circuit 48, the signal processor 44, the coordinate extractor 45, and the image processor 49 so as to operate in synchronization with one another.

The detection circuit 48 is, for example, an analog front-end (AFE) circuit. The detection circuit 48 is a signal processing circuit having functions of at least a detection signal amplifier 42 and an analog-to-digital (A/D) converter 43. The detection signal amplifier 42 amplifies the detection signal Vdet. The A/D converter 43 converts an analog signal output from the detection signal amplifier 42 into a digital signal.

The signal processor 44 is a logic circuit that detects a predetermined physical quantity received by the sensor 10 based on an output signal of the detection circuit 48. The signal processor 44 can detect the asperities on the surface of the finger Fg or the palm based on the signals from the detection circuit 48 when the finger Fg is in contact with or in proximity to a detection surface. The signal processor 44 can also detect the information on the living body based on the signals from the detection circuit 48. Examples of the information on the living body include the vascular image, the pulse waves, the pulsation, and the blood oxygen level of the finger Fg or the palm.

The signal processor 44 may also perform processing of acquiring the detection signals Vdet (information on the living body) simultaneously detected by the optical sensors PD, and averaging the detection signals Vdet. In this case, the detector 40 can perform stable detection by reducing measurement errors caused by noise or relative positional misalignment between the object to be detected, such as the finger Fg, and the sensor 10.

The storage 46 temporarily stores therein signals calculated by the signal processor 44. The storage 46 may be, for example, a random-access memory (RAM) or a register circuit.

The coordinate extractor 45 is a logic circuit that obtains detected coordinates of the asperities on the surface of the finger or the like when the contact or the proximity of the finger is detected by the signal processor 44. The coordinate extractor 45 is the logic circuit that also obtains detected coordinates of blood vessels of the finger Fg or the palm. The image processor 49 combines the detection signals Vdet output from the respective optical sensors PD of the sensor 10 to generate two-dimensional information indicating the shape of the asperities on the surface of the finger Fg or the like and two-dimensional information indicating the shape of the blood vessels of the finger Fg or the palm. The coordinate extractor 45 may output the detection signals Vdet as sensor output voltages Vo instead of calculating the detected coordinates. A case can be considered where the detector 40 does not include the coordinate extractor 45 and the image processor 49.

The output processor 50 serves as a processor that performs processing based on the outputs from the optical sensors PD. Specifically, the output processor 50 of the present embodiment outputs the sensor output voltages Vo including at least the pulse wave data based on at least the detection signals Vdet acquired through the signal processor 44. In the present embodiment, the signal processor 44 outputs data indicating a variation (amplitude) in output voltage of the detection signal Vdet of each of the optical sensors PD (described later), and the output processor 50 determines which outputs are to be employed as the sensor output voltages Vo. However, the signal processor 44 or the output processor 50 may perform both these operations. The output processor 50 may include, for example, the detected coordinates obtained by the coordinate extractor 45 and the two-dimensional information generated by the image processor 49 in the sensor output voltages Vo. The function of the output processor 50 may be integrated into another component (for example, the image processor 49).

The following describes a circuit configuration example of the detection device 1. FIG. 3 is a circuit diagram illustrating the detection device. As illustrated in FIG. 3, the sensor 10 has a plurality of partial detection areas PAA arranged in a matrix having a row-column configuration. Each of the partial detection areas PAA is provided with the optical sensor PD. That is, the optical sensors PD are arranged in a matrix having a row-column configuration on the sensor base member 21.

The gate lines GCL extend in the first direction Dx, and are each electrically coupled to the partial detection areas PAA arranged in the first direction Dx. A plurality of gate lines GCL(1), GCL(2), . . . , GCL(8) are arranged in the second direction Dy and are each electrically coupled to the gate line drive circuit 15. In the following description, the gate lines GCL(1), GCL(2), . . . , GCL(8) will each be simply referred to as the gate line GCL when they need not be distinguished from one another. For ease of understanding of the description, FIG. 3 illustrates eight of the gate lines GCL. However, this is merely an example, and M gate lines GCL (where M is 8 or larger, and is, for example, 256) may be arranged.

The signal lines SGL extend in the second direction Dy and are each electrically coupled to the optical sensors PD of the partial detection areas PAA arranged in the second direction Dy. A plurality of signal lines SGL(1), SGL(2), . . . , SGL(12) are arranged in the first direction Dx and are each electrically coupled to the signal line selection circuit 16 and a reset circuit 17. In the following description, the signal lines SGL(1), SGL(2), . . . , SGL(12) will each be simply referred to as the signal line SGL when they need not be distinguished from one another.

For ease of understanding of the description, 12 of the signal lines SGL are illustrated. However, this is merely an example, and N signal lines SGL (where N is 12 or larger, and is, for example, equal to 252) may be arranged.

In FIG. 3, the sensor 10 is provided between the signal line selection circuit 16 and the reset circuit 17. The present disclosure is not limited thereto. The signal line selection circuit 16 and the reset circuit 17 may be electrically coupled to ends of the signal lines SGL in the same direction. The substantial area of one sensor is, for example, substantially 50×50 μm². The resolution of the detection area AA is, for example, substantially 508 pixels per inch (ppi). The number of the sensors arranged in the detection area AA is, for example, 252 cells×256 cells. The area of the detection area AA is, for example, 12.6×12.8 mm².

The gate line drive circuit 15 receives the various control signals such as the start signal STV, the clock signal CK, and the reset signal RST1 from the control circuit 122 (refer to FIG. 1). The gate line drive circuit 15 sequentially selects the gate lines GCL(1), GCL(2), . . . , GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr electrically coupled to the gate line GCL, and corresponding ones of the partial detection areas PAA arranged in the first direction Dx are selected as detection targets.

The gate line drive circuit 15 may perform different driving for each of detection modes including the detection of the fingerprint and the detection of different items of the information on the living body (such as the pulse waves, the pulsation, the vascular image, and the blood oxygen level). For example, the gate line drive circuit 15 may collectively drive more than one of the gate lines GCL.

The signal line selection circuit 16 includes a plurality of selection signal lines Lsel, a plurality of output signal lines Lout, and third switching elements TrS. The third switching elements TrS are provided correspondingly to the signal lines SGL. Six signal lines SGL(1), SGL(2), . . . , SGL(6) are electrically coupled to a common output signal line Lout1. Six signal lines SGL(7), SGL(8), . . . , SGL(12) are electrically coupled to a common output signal line Lout2. The output signal lines Lout1 and Lout2 are each electrically coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are electrically coupled to the gates of the respective third switching elements TrS included in one of the signal line blocks. One of the selection signal lines Lsel is electrically coupled to the gates of the third switching elements TrS in the signal line blocks.

The control circuit 122 (refer to FIG. 1) sequentially supplies the selection signal ASW to the selection signal lines Lsel. This operation causes the signal line selection circuit 16 to operate the third switching elements TrS to sequentially select the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs. The signal line selection circuit 16 may collectively couple more than one of the signal lines SGL to the detection circuit 48 electrically.

As illustrated in FIG. 3, the reset circuit 17 includes a reference signal line Lvr, a reset signal line Lrst, and fourth switching elements TrR. The fourth switching elements TrR are provided correspondingly to the signal lines SGL. The reference signal line Lvr is electrically coupled to either the sources or the drains of the fourth switching elements TrR. The reset signal line Lrst is electrically coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference potential COM to the reference signal line Lvr. This operation supplies the reference potential COM to a capacitive element Ca (refer to FIG. 4) included in each of the partial detection areas PAA.

Figure 4:
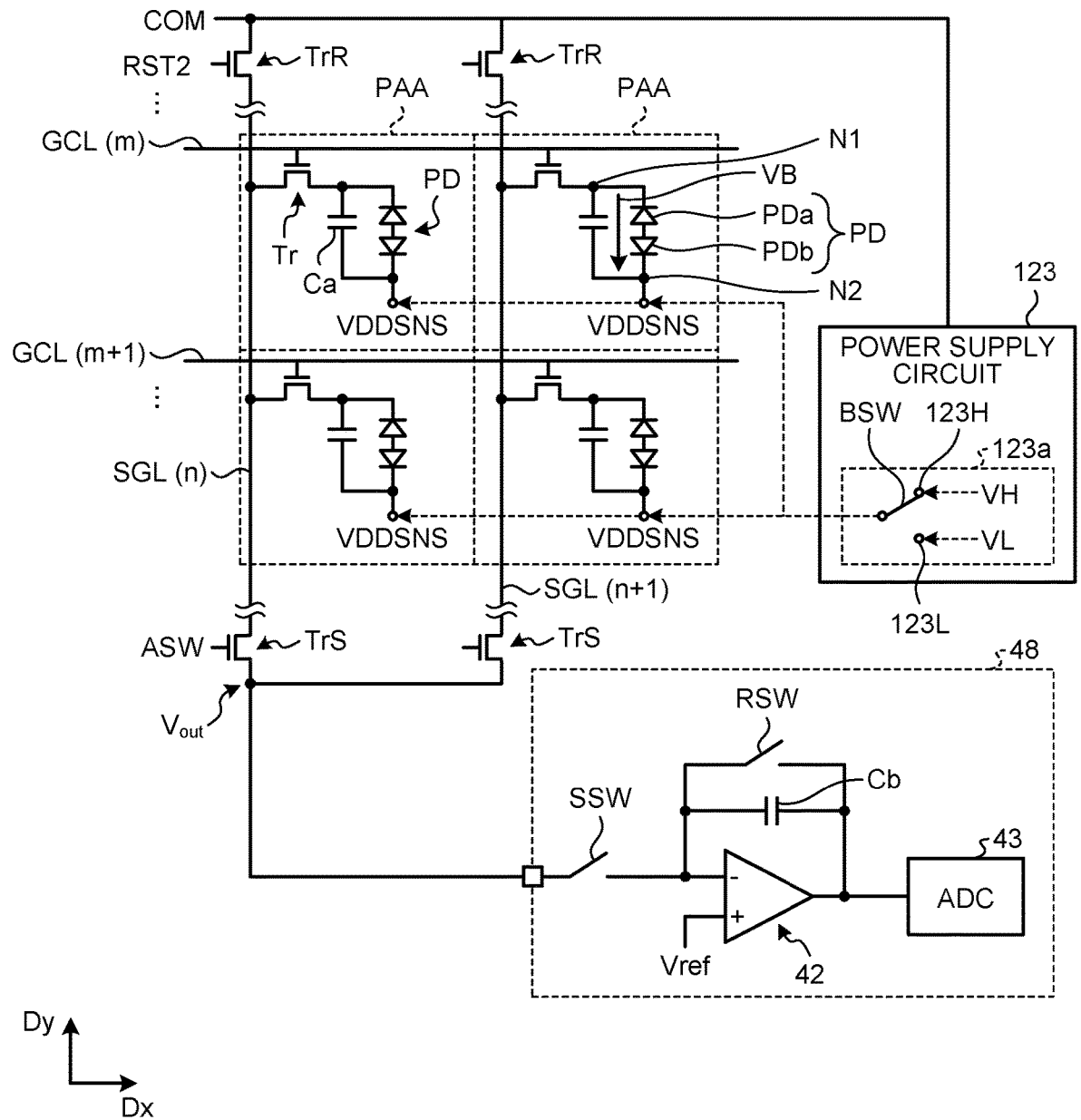
FIG. 4 is a circuit diagram illustrating a plurality of partial detection areas.

FIG. 4 is a circuit diagram illustrating the partial detection areas. FIG. 4 also illustrates a circuit configuration of the detection circuit 48. As illustrated in FIG. 4, each of the partial detection areas PAA includes the optical sensor PD, the capacitive element Ca, and a corresponding one of the first switching elements Tr. The capacitive element Ca is capacitance (sensor capacitance) generated in the optical sensor PD and is equivalently electrically coupled in parallel to the optical sensor PD.

FIG. 4 illustrates two gate lines GCL(m) and GCL(m+1) arranged in the second direction Dy among the gate lines GCL. FIG. 4 also illustrates two signal lines SGL(n) and SGL(n+1) arranged in the first direction Dx among the signal lines SGL. The partial detection area PAA is an area surrounded by the gate lines GCL and the signal lines SGL.

The first switching elements Tr are provided corresponding to the optical sensors PD. Each of the first switching elements Tr is formed of a thin-film transistor, and in this example, formed of an n-channel metal oxide semiconductor (MOS) thin-film transistor (TFT).

The gates of the first switching elements Tr belonging to the partial detection areas PAA arranged in the first direction Dx are electrically coupled to the gate line GCL. The sources of the first switching elements Tr belonging to the partial detection areas PAA arranged in the second direction Dy are electrically coupled to the signal line SGL. The drain of the first switching element Tr is electrically coupled to a first terminal N1 on one end side of the optical sensor PD and the capacitive element Ca.

The optical sensor PD includes the first photodiode PDa and the second photodiode PDb. The first photodiode PDa and the second photodiode PDb are coupled in series and in opposite directions between the first terminal N1 on the one end side and a second terminal N2 on the other end side of the optical sensor PD. The term "coupled in opposite directions" indicates a coupling configuration in which rectification characteristics of the first photodiode PDa and the second photodiode PDb are in directions opposite to each other. More specifically, the cathode of the first photodiode PDa is electrically coupled to the first terminal N1; the anode of the first photodiode PDa is electrically coupled to the anode of the second photodiode PDb; and the cathode of the second photodiode PDb is electrically coupled to the second terminal N2.

The second terminal N2 of the optical sensor PD (the cathode of the second photodiode PDb) is supplied with the drive signal VDDSNS from a drive signal supply circuit 123*a*. The drive signal supply circuit 123*a* is provided in the power supply circuit 123. The drive signal supply circuit 123*a* is not limited to being provided therein, but may be provided in the control circuit 122 or on the sensor base member 21. The signal line SGL and the first terminal N1 (the capacitive element Ca and the optical sensor PD) are supplied, from the power supply circuit 123, with the reference potential COM that serves as an initial potential of the signal line SGL and the first terminal N1 (the capacitive element Ca and the optical sensor PD). With the drive signal VDDSNS and the reference potential COM, a bias voltage VB is supplied to the optical sensor PD. The bias voltage VB is expressed as VB=COM−VDDSNS.

The drive signal supply circuit 123a that supplies the drive signal VDDSNS to the optical sensor PD includes a first voltage signal supply 123H, a second voltage signal supply 123L, and a switch BSW. The first voltage signal supply 123H is a circuit that supplies a first voltage signal VH having a higher level voltage than the reference potential COM. The second voltage signal supply 123L is a circuit that supplies a second voltage signal VL having a lower level voltage than the reference potential COM. The switch BSW is a switch element that switches the coupling state of the first voltage signal supply 123H and the second voltage signal supply 123L to the second terminal N2 of the optical sensor PD. By operating the switch BSW, the drive signal supply circuit 123a supplies the first voltage signal VH and the second voltage signal VL to the second terminal N2 of the optical sensor PD in a time-division manner.

When the first voltage signal VH (VH>COM) is supplied from the drive signal supply circuit 123a to the second terminal N2 of the optical sensor PD, the first photodiode PDa is driven in a forward biased state and the second photodiode PDb is driven in a reverse biased state. In this case, the second photodiode PDb performs the detection, and a forward current flows through the first photodiode PDa. For example, the reference potential COM is set to 0.75 V, and the first voltage signal VH is set to 2.75 V. In this case, the bias voltage VB is expressed as VB=0.75−2.75=−2.0 V.

When the second voltage signal VL (VL<COM) is supplied from the drive signal supply circuit 123a to the second terminal N2 of the optical sensor PD, the first photodiode PDa is driven in the reverse biased state, and the second photodiode PDb is driven in the forward biased state. In this case, the first photodiode PDa performs the detection, and a forward current flows through the second photodiode PDb. For example, the reference potential COM is set to 0.75 V, and the second voltage signal VL is set to −1.25 V. In this case, the bias voltage VB expressed as VB=0.75−(−1.25)=+2.0 V.

When the partial detection area PAA is irradiated with light, a current corresponding to the amount of the light flows through the optical sensor PD (the first photodiode PDa or the second photodiode PDb). As a result, an electric charge is stored in the capacitive element Ca. After the first switching element Tr is turned on, a current corresponding to the electric charge stored in the capacitive element Ca flows through the signal line SGL. The signal line SGL is electrically coupled to the detection circuit 48 through a corresponding one of the third switching elements TrS of the signal line selection circuit 16. Thus, the detection device 1 can detect a signal corresponding to the amount of the light received by the optical sensor PD in each of the partial detection areas PAA or for each block unit PAG.

During a read period Pdet (refer to FIG. 7), a switch SSW of the detection circuit 48 is turned on, and the detection circuit 48 is electrically coupled to the signal lines SGL. The detection signal amplifier 42 of the detection circuit 48 converts a current supplied from the signal line SGL into a voltage corresponding to the value of the current, and amplifies the result. A reference potential (Vref) having a fixed potential is supplied to a non-inverting input portion (+) of the detection signal amplifier 42, and the signal lines SGL are electrically coupled to an inverting input portion (−) of the detection signal amplifier 42. In the present embodiment, the same signal as the reference potential COM is supplied as the reference potential (Vref) voltage. The signal processor 44 (refer to FIG. 2) calculates the difference between the detection signal Vdet when the optical sensor PD is irradiated by light and the detection signal Vdet when the optical sensor PD is not irradiated by light, as each of the sensor output voltages Vo. The detection signal amplifier 42 includes a capacitive element Cb and a reset switch RSW. During a reset period Prst (refer to FIG. 7), the reset switch RSW is turned on, and the electric charge of the capacitive element Cb is reset.

If variations are present in the organic semiconductor layer where the optical sensor PD (organic photodiode (OPD)) is formed, the characteristics of the OPD may vary to reduce the detection accuracy. The following describes the diode characteristics of the optical sensor PD when variations are present in the organic semiconductor layer, with reference to FIG. 5.

Figure 5:
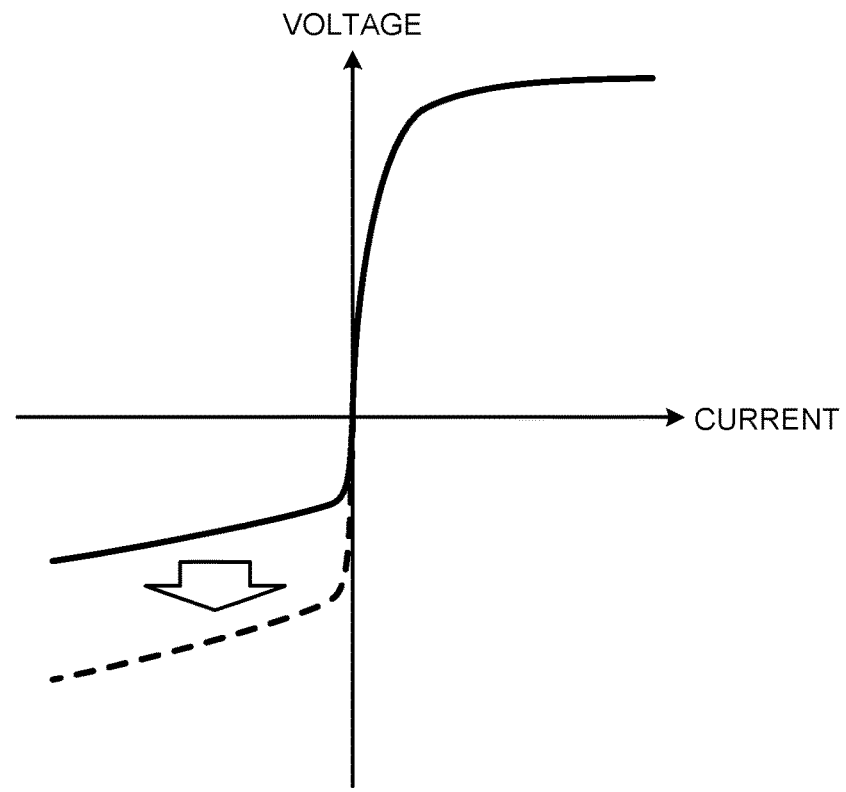
FIG. 5 is a diagram illustrating exemplary diode characteristics of an optical sensor.

FIG. 5 is a diagram illustrating an example of the diode characteristics of the optical sensor. In FIG. 5, the horizontal axis represents the current, and the vertical axis represents the voltage. In FIG. 5, the solid line indicates the diode characteristics under normal conditions, and the dashed line indicates an example of a change in the characteristics due to variations in characteristics of the OPD.

The variations in the organic semiconductor layer where the optical sensor PD (organic photodiode (OPD)) is formed may cause a change in reverse characteristics of the OPD as illustrated with the dashed line. As a result, a reverse current flowing through the optical sensor PD during an exposure period (effective exposure period) (described below) varies for each of the partial detection areas PAA, resulting in a reduction in detection accuracy.

In the present embodiment, the characteristics of the OPD are returned to the initial state (solid line illustrated in FIG. 5) by applying a forward bias current to the optical sensor PD at predetermined timing. In the present disclosure, this operation to return the characteristics of the OPD to the initial state is called "refreshing operation".

Figure 6:
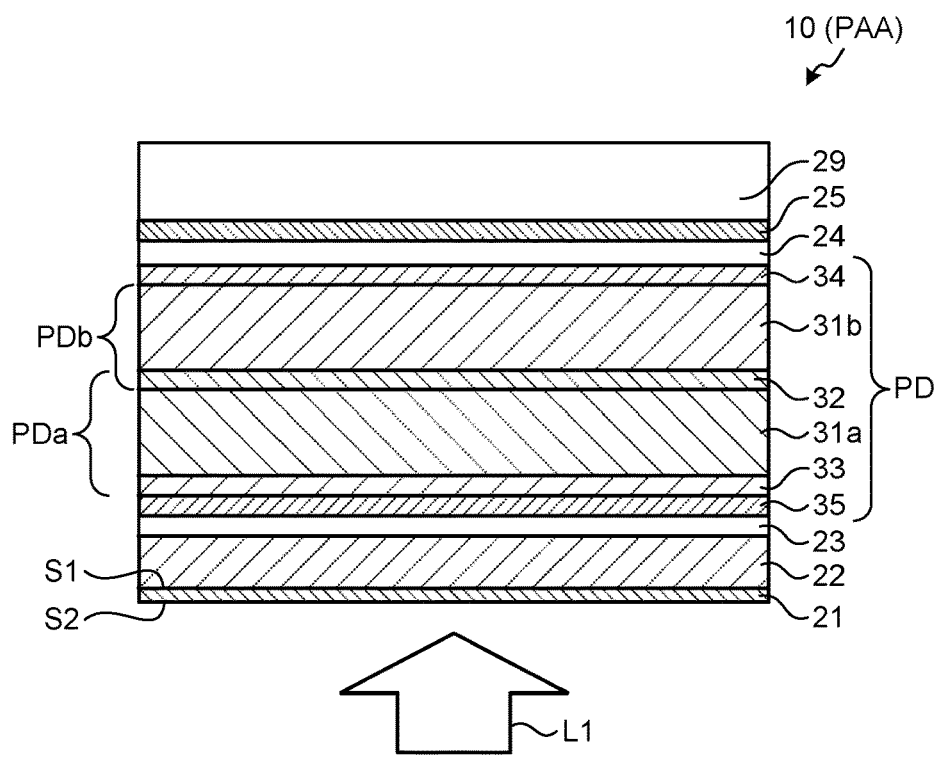
FIG. 6 is a sectional view illustrating a schematic sectional configuration of a sensor.

The following describes a configuration example of the optical sensor PD. FIG. 6 is a sectional view illustrating a schematic sectional configuration of the sensor. As illustrated in FIG. 6, the sensor 10 includes the sensor base member 21, a TFT layer 22, an insulating layer 23, the optical sensor PD, an intermediate layer 24, a sealing layer 25, and a protective layer 29. The sensor base member 21 is an insulating base member and is made using, for example, glass or a resin material. The sensor base member 21 is not limited to having a flat plate shape but may have a curved surface. In this case, the sensor base member 21 can be a film-like resin. The sensor base member 21 has a first surface S1 and a second surface S2 opposite the first surface. The TFT layer 22, the insulating layer 23, the optical sensor PD, the intermediate layer 24, the sealing layer 25, and the protective layer 29 are stacked in this order on the first surface S1. In the present embodiment, a configuration will be described in which light L1 is applied to the optical sensor PD from the second surface S2 side. However, the configuration is not limited thereto, but the light L1 may be applied to the optical sensor PD from the first surface S1 side.

The TFT layer 22 is provided with circuits such as the gate line drive circuit 15 and the signal line selection circuit 16 described above. The TFT layer 22 is also provided with TFTs, such as the first switching elements Tr, and various types of wiring, such as the gate lines GCL and the signal lines SGL. The sensor base member 21 and the TFT layer 22 serve as a drive circuit board that drives the sensor for each predetermined detection area, and are also called a backplane or an array substrate.

The insulating layer 23 is an organic insulating layer and is provided above the TFT layer 22. The insulating layer 23 is a planarizing layer that planarizes asperities formed by the first switching elements Tr and various conductive layers formed in the TFT layer 22.

The optical sensor PD is provided on the insulating layer 23. The optical sensor PD is configured such that the first photodiode PDa and the second photodiode PDb are stacked on the insulating layer 23 in the order as listed. More specifically, the optical sensor PD is configured such that a lower electrode 35 (first electrode), an electron transport layer 33, a first active layer 31a, a hole transport layer 32, a second active layer 31b, and an upper electrode 34 (second electrode) are stacked in the order as listed, in a normal direction of the first surface S1 of the sensor base member 21.

The lower electrode 35 is provided on the insulating layer 23 and is electrically coupled to the first switching element Tr in the TFT layer 22 through a contact hole (not illustrated). The lower electrode 35 is the cathode (first terminal N1) of the first photodiode PDa, and is an electrode for reading the detection signal Vdet. The lower electrode 35 is formed of, for example, a light-transmitting conductive material such as indium tin oxide (ITO).

The first and the second active layers 31a and 31b change in characteristics (for example, voltage-current characteristics and resistance values) according to light emitted thereto. An organic material is used as a material of the first and the second active layers 31a and 31b. Specifically, the first and the second active layers 31a and 31b have a bulk heterostructure in which a p-type organic semiconductor is mixed with an n-type fullerene derivative (PCBM) that is an n-type organic semiconductor. As the first and the second active layers 31a and 31b, low-molecular-weight organic materials can be used including, for example, fullerene ($C_{60}$), (6,6)-phenyl-$C_{61}$-butyric acid methyl ester (PCBM), copper phthalocyanine (CuPc), fluorinated copper phthalocyanine ($F_{16}$CuPc), 5,6,11,12-tetraphenyltetracene (rubrene), and perylene diimide (PDI) (derivative of perylene).

The first and the second active layers 31a and 31b can be formed by a vapor deposition process (dry process) using the low-molecular-weight organic materials listed above. In this case, the first and the second active layers 31a and 31b may be, for example, multilayered films of CuPc and $F_{16}$CuPc, or multilayered films of rubrene and $C_{60}$. The first and the second active layers 31a and 31b can also be formed by a coating process (wet process). In this case, the first and the second active layers 31a and 31b are made using a material obtained by combining the above-listed low-molecular-weight organic materials with high-molecular-weight organic materials. As the high-molecular-weight organic materials, for example, poly(3-hexylthiophene) (P3HT) and F8-alt-benzothiadiazole (F8BT) can be used. The first and the second active layers 31a and 31b can be films in the state of a mixture of P3HT and PCBM or films in the state of a mixture of F8BT and PDI.

The first and the second active layers 31a and 31b may be formed of the same material or different materials. For example, P3HT:PCBM (a film in the state of a mixture of P3HT and PCBM) can be used as the first active layer 31a poly((2,5-bis(2-hexyldecyl)-2,3,5,6-tetrahydro-3,6-dioxopyrrolo(3,4-c)pyrrole-1,4-diyl)-alt-(3',3"-dimethyl-2,2': 5',2"-terthiophene)-5,5"-diyl) (PMDPP3T):(6,6)-Phenyl $C_{61}$ butyric acid methyl ester (PCBM) (a film in the state of a mixture of PMDPP3T and PCBM) can be used as the second active layer 31b. In this case, the first photodiode PDa is sensitive to visible light (with a wavelength of, for example, from 400 nm to 650 nm). The second photodiode PDb is sensitive to near-infrared light (with a wavelength of, for example, from 780 nm to 950 nm).

The upper electrode 34 is the cathode (second terminal N2) of the second photodiode PDb and is an electrode for supplying the drive signal VDDSNS to the optical sensor PD. The upper electrode 34 faces the lower electrode 35 with the first and the second active layers 31a and 31b interposed therebetween. For example, aluminum (Al) is used as the upper electrode 34. Alternatively, the upper electrode 34 may be a metal material such as silver (Ag) or an alloy material containing at least one or more of these metal materials.

The electron transport layer 33 and the hole transport layer 32 are provided to facilitate holes and electrons generated in the first and the second active layers 31a and 31b to reach the upper electrode 34 or the lower electrode 35. The electron transport layer 33 is provided between the lower electrode 35 and the first active layer 31a in the normal direction of the first surface S1 of the sensor base member 21. The electron transport layer 33 is in direct contact with the top of the lower electrode 35, and the first active layer 31a is in direct contact with the top of the electron transport layer 33. Polyethylenimine ethoxylated (PEIE) or zinc oxide (ZnO) is used as a material of the electron transport layer 33.

The hole transport layer 32 is provided between the first and the second active layers 31a and 31b in the normal direction of the first surface S1 of the sensor base member 21. The hole transport layer 32 is in direct contact with the top of the first active layer 31a, and the second active layer 31b is in direct contact with the top of the hole transport layer 32. A polythiophene-based conductive polymer (poly (3,4-ethylenedioxythiophene) (PEDOT)):poly(styrene sulfonate) (PSS) is used as the hole transport layer 32. In the present embodiment, the hole transport layer 32 is shared by the first and the second photodiodes PDa and PDb.

The sealing layer 25 is provided so as to cover the optical sensor PD. More specifically, the sealing layer 25 is provided above the upper electrode 34 with the intermediate layer 24 interposed therebetween. The material of the sealing layer 25 is aluminum oxide ($Al_2O_3$). This configuration allows the detection device 1 to seal the optical sensor PD better than in a case of using parylene as the sealing layer 25. ITO is used as a material of the intermediate layer 24. The intermediate layer 24 can improve the adhesion between the upper electrode 34 and the sealing layer 25.

The protective layer 29 is provided so as to cover the sealing layer 25. For example, a resin film is used as the protective layer 29. The protective layer 29 is provided to protect the optical sensor PD. The material of the protective layer 29 is not limited to a resin film, but other materials may be used.

In the present embodiment, the configuration has been described in which the light L1 is applied to the optical sensor PD from the second surface S2 side. However, the configuration may be such that the light L1 is applied to the optical sensor PD from the first surface S1 side. In this case, a light-transmitting conductive material such as ITO is used as the upper electrode 34, and a metal material such as aluminum or silver is used as the lower electrode 35.

Figure 7:
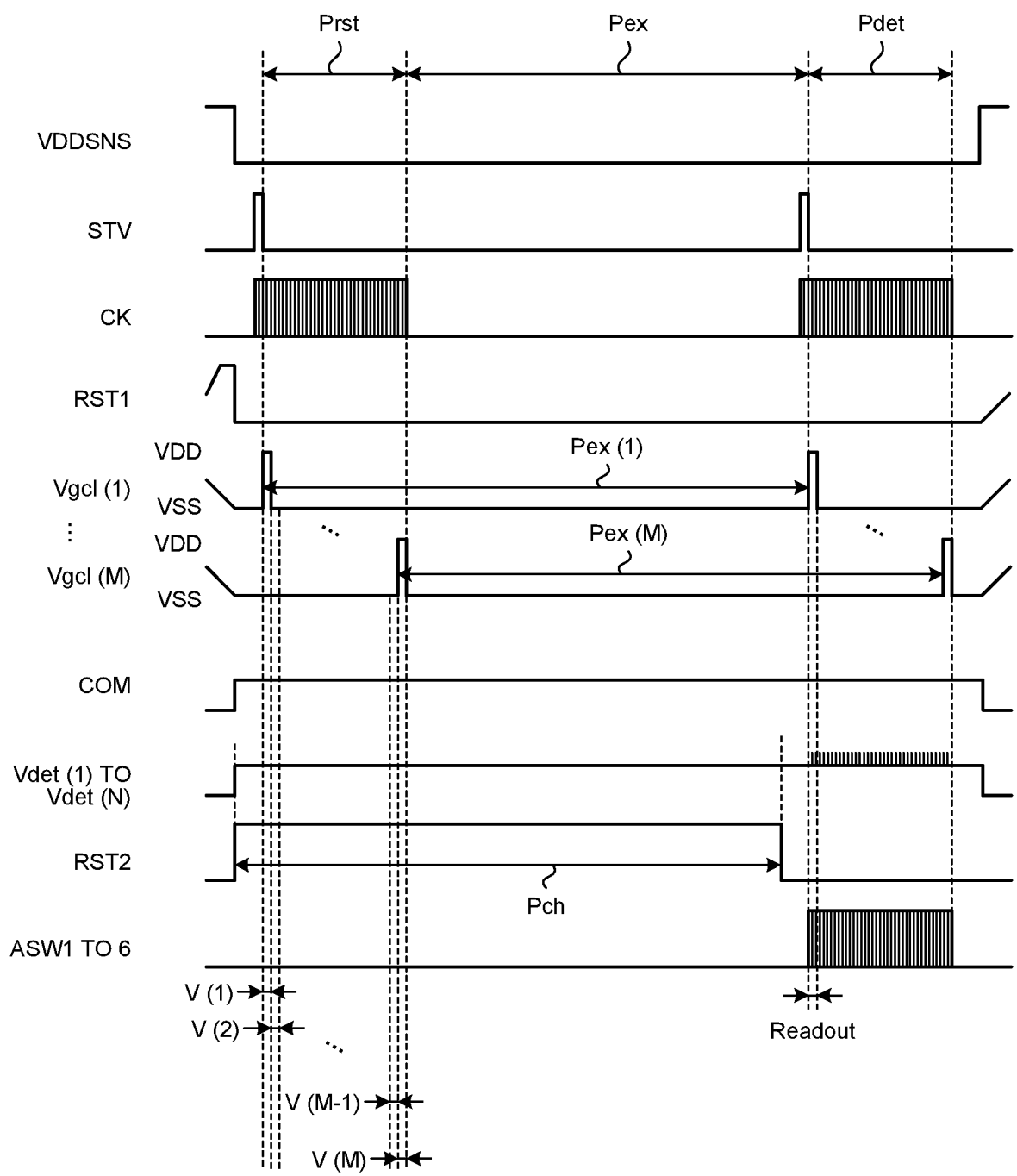
FIG. 7 is a waveform timing chart illustrating an operation example of the detection device.

The following describes an operation example of the detection device 1. FIG. 7 is a waveform timing chart illustrating the operation example of the detection device.

FIG. 7 illustrates the case where the second voltage signal VL is mainly supplied as the drive signal VDDSNS, that is, the case where the first photodiode PDa of the optical sensor PD performs the detection. However, the explanation in FIG. 7 can also be applied to the case where the first voltage signal VH is supplied as the drive signal VDDSNS, that is, the case of the detection by the second photodiode PDb of the optical sensor PD.

As illustrated in FIG. 7, the detection device 1 has the reset period Prst, an exposure period Pex, and the read period Pdet. The power supply circuit 123 (drive signal supply circuit 123a) supplies the drive signal VDDSNS to the anode of the optical sensor PD over the reset period Prst, the exposure period Pex, and the read period Pdet. The drive signal VDDSNS is a signal that applies the bias voltage VB between the first terminal N1 and the second terminal N2 of the optical sensor PD. For example, the reference potential COM of substantially 0.75 V is applied to the first terminal N1 of the optical sensor PD. By applying the drive signal VDDSNS of substantially −1.25 V to the second terminal N2, the bias voltage VB of substantially 2.0 V is supplied between the first terminal N1 and the second terminal N2. The control circuit 122 sets the reset signal RST2 to "H", and then, supplies the start signal STV and the clock signal CK to the gate line drive circuit 15 to start the reset period Prst. During the reset period Prst, the control circuit 122 supplies the reference potential COM to the reset circuit 17, and uses the reset signal RST2 to turn on the fourth switching elements TrR for supplying a reset voltage. This operation supplies the reference potential COM as the reset voltage to each of the signal lines SGL.

During the reset period Prst, the gate line drive circuit 15 sequentially selects each of the gate lines GCL based on the start signal STV, the clock signal CK, and the reset signal RST1. The gate line drive circuit 15 sequentially supplies gate drive signals Vgcl {Vgcl(1), ..., Vgcl(M)} to the gate lines GCL. Each of the gate drive signals Vgcl has a pulsed waveform having a power supply voltage VDD serving as a high-level voltage and a power supply voltage VSS serving as a low-level voltage. In FIG. 7, M gate lines GCL (where M is, for example, 256) are provided, and the gate drive signals Vgcl(1), ..., Vgcl(M) are sequentially supplied to the respective gate lines GCL. Thus, the first switching elements Tr are sequentially brought into a conducting state and supplied with the reset voltage on a row-by-row basis. For example, the reference potential COM having a voltage of 0.75 V is supplied as the reset voltage.

Thus, during the reset period Prst, the capacitive elements Ca of all the partial detection areas PAA are sequentially electrically coupled to the signal lines SGL, and are supplied with the reference potential COM. As a result, the capacitance of the capacitive elements Ca is reset. The capacitance of the capacitive elements Ca of some of the partial detection areas PAA can be reset by partially selecting the gate lines and the signal lines SGL.

Examples of the method of controlling the exposure include a method of controlling the exposure during non-selection of the gate lines and a method of always controlling the exposure. In the method of controlling the exposure during non-selection of the gate lines, the gate drive signals {Vgcl(1), ..., Vgcl(M)} are sequentially supplied to all the gate lines GCL electrically coupled to the optical sensors PD serving as the detection targets, and all the optical sensors PD serving as the detection targets are supplied with the reset voltage. Then, after all the gate lines GCL electrically coupled to the optical sensors PD serving as the detection targets are set to a low voltage (the first switching elements Tr are turned off), the exposure starts and the exposure is performed during the exposure period Pex. After the exposure ends, the gate drive signals {Vgcl(1), ..., Vgcl(M)} are sequentially supplied to the gate lines GCL electrically coupled to the optical sensors PD serving as the detection targets as described above, and reading is performed during the read period Pdet. In the method of always controlling the exposure, the control for performing the exposure can also be performed during the reset period Prst and the read period Pdet (the exposure is always controlled). In this case, an effective exposure period SPex(1) starts immediately after the gate drive signal Vgcl(1) is supplied to the gate line GCL in the reset period Prst. Herein, effective exposure periods SPex(1), ..., SPex(M) are periods during which the capacitive elements Ca are charged from the optical sensors PD. That is, in the method of always controlling the exposure, each of the effective exposure periods SPex starts when the first switching element Tr is turned off. The electric charge stored in the capacitive element Ca during the reset period Prst flows as a reverse directional current (from cathode to anode) through the optical sensor PD due to light irradiation, and the potential difference in the capacitive element Ca decreases. The start timing and the end timing of the actual effective exposure periods SPex(1), ..., SPex(M) are different among the partial detection areas PAA corresponding to the respective gate lines GCL. Each of the effective exposure periods SPex(1), ..., SPex(M) starts when the gate drive signal Vgcl changes from the power supply voltage VDD serving as the high-level voltage to the power supply voltage VSS serving as the low-level voltage in the reset period Prst. Each of the effective exposure periods SPex(1), ..., SPex(M) ends when the gate drive signal Vgcl changes from the power supply voltage VSS to the power supply voltage VDD in the read period Pdet. The lengths of the effective exposure periods SPex(1), ..., SPex(M) are equal.

In the method of controlling the exposure during non-selection of the gate lines, a current flows correspondingly to the light received by the optical sensor PD in each of the partial detection areas PAA during the exposure periods Pex {(1) ... (M)}. As a result, an electric charge is stored in each of the capacitive elements Ca.

At a time before the read period Pdet starts, the control circuit 122 sets the reset signal RST2 to a low-level voltage. This operation stops the operation of the reset circuit 17. The reset signal may be set to a high-level voltage only during the reset period Prst. During the read period Pdet, the gate line drive circuit 15 sequentially supplies the gate drive signals Vgcl(1), ..., Vgcl(M) to the gate lines GCL in the same manner as during the reset period Prst.

Specifically, the gate line drive circuit 15 supplies the gate drive signal Vgcl(1) at the high-level voltage (power supply voltage VDD) to the gate line GCL(1) during a period V(1). The control circuit 122 sequentially supplies the selection signals ASW1, ..., ASW6 to the signal line selection circuit 16 during a period in which the gate drive signal Vgcl(1) is at the high-level voltage (power supply voltage VDD). This operation sequentially or simultaneously electrically couples the signal lines SGL of the partial detection areas PAA selected by the gate drive signal Vgcl(1) to the detection circuit 48. As a result, the detection signal Vdet for each of the partial detection areas PAA is supplied to the detection circuit 48.

In the same manner, the gate line drive circuit 15 supplies the gate drive signals Vgcl(2), ..., Vgcl(M−1), Vgcl(M) at the high-level voltage to gate lines GCL(2), ..., GCL(M−1), GCL(M) during periods V(2), ..., V(M−1), V(M), respectively. That is, the gate line drive circuit 15 supplies the gate drive signal Vgcl to the gate line GCL during each of the periods V(1), V(2), . . . , V(M−1), V(M). The signal line selection circuit 16 sequentially selects each of the signal lines SGL based on the selection signal ASW in each period in which the gate drive signal Vgcl is set to the high-level voltage. The signal line selection circuit 16 sequentially electrically couples each of the signal lines SGL to one detection circuit 48. Thus, the detection device 1 can output the detection signals Vdet of all the partial detection areas PAA to the detection circuit 48 during the read period Pdet.

Figure 8:
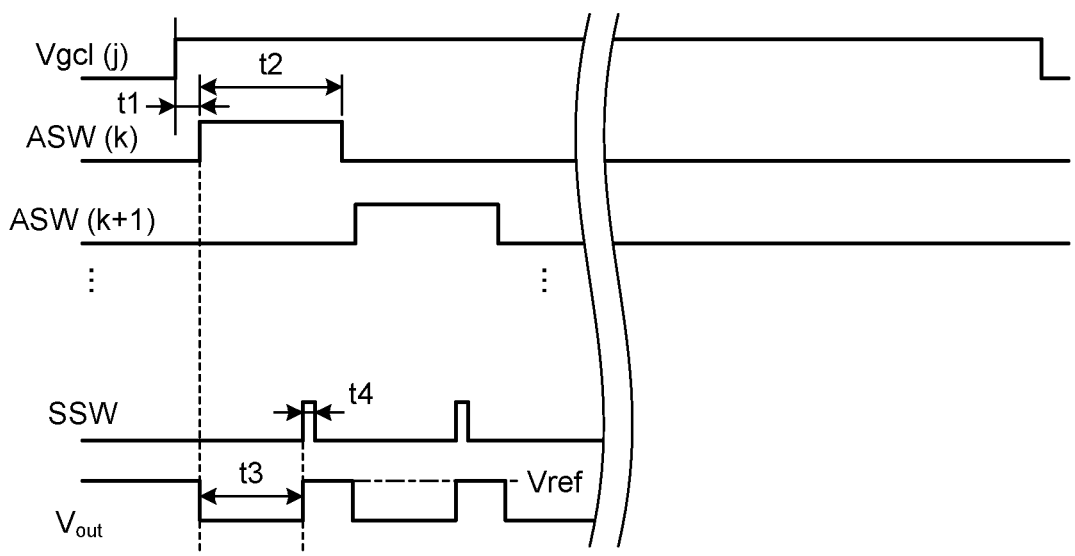
FIG. 8 is a waveform timing chart illustrating an operation example during a read period in FIG. 7.

FIG. 8 is a waveform timing chart illustrating an operation example during the read period in FIG. 7. With reference to FIG. 8, the following describes the operation example during a supply period Readout of one gate drive signal Vgcl(j) in FIG. 7. In FIG. 7, the reference numeral of the supply period Readout is assigned to the first gate drive signal Vgcl(1), and the same applies to the other gate drive signals Vgcl(2), . . . , Vgcl(M). The index j is any one of the natural numbers 1 to M.

As illustrated in FIGS. 8 and 4, an output voltage ($V_{out}$) of each of the third switching elements TrS has been reset to the reference potential (Vref) voltage in advance. The reference potential (Vref) voltage serves as the reset voltage, and is set to 0.75 V, for example. Then, the gate drive signal Vgcl(j) is set to a high level, and the first switching elements Tr of a corresponding row are turned on. Thus, each of the signal lines SGL in each row is set to a voltage corresponding to the electric charge stored in the capacitor (capacitive element Ca) of the partial detection area PAA. After a period t1 elapses from a rising edge of the gate drive signal Vgcl(j), a period t2 starts in which the selection signal ASW(k) is set to a high level. After the selection signal ASW(k) is set to the high level and the third switching element TrS is turned on, the electric charge stored in the capacitor (capacitive element Ca) of the partial detection area PAA electrically coupled to the detection circuit 48 through the third switching element TrS changes the output voltage ($V_{out}$) of the third switching element TrS (refer to FIG. 4) to a voltage corresponding to the electric charge stored in the capacitor (capacitive element Ca) of the partial detection area PAA (period t3). In the example of FIG. 8, this voltage is reduced from the reset voltage as illustrated in the period t3. Then, after the switch SSW is turned on (in a period t4 during which an SSW signal is set to a high level), the electric charge stored in the capacitor (capacitive element Ca) of the partial detection area PAA moves to the capacitor (capacitive element Cb) of the detection signal amplifier 42 of the detection circuit 48, and the output voltage of the detection signal amplifier 42 is set to a voltage corresponding to the electric charge stored in the capacitive element Cb. At this time, the potential of the inverting input portion of the detection signal amplifier 42 is set to an imaginary short-circuit potential of an operational amplifier, and therefore, set to the reference potential (Vref). The A/D converter 43 reads the output voltage of the detection signal amplifier 42. In the example of FIG. 8, waveforms of the selection signals ASW(k), ASW(k+1), . . . corresponding to the signal lines SGL of the respective columns are set to a high level to sequentially turn on the third switching elements TrS, and the same operation is sequentially performed to sequentially read the electric charges stored in the capacitors (capacitive elements Ca) of the partial detection areas PAA electrically coupled to the gate line GCL. ASW(k), ASW(k+1), . . . in FIG. 8 are, for example, any of ASW1 to ASW6 in FIG. 3.

Specifically, after the period t4 starts in which the switch SSW is on, the electric charge moves from the capacitor (capacitive element Ca) of the partial detection area PAA to the capacitor (capacitive element Cb) of the detection signal amplifier 42 of the detection circuit 48. At this time, the non-inverting input (+) of the detection signal amplifier 42 is set to the reference potential (Vref) voltage (for example, 0.75 V). As a result, the output voltage ($V_{out}$) of the third switching element TrS is also set to the reference potential (Vref) voltage due to the imaginary short-circuit between the input ends of the detection signal amplifier 42. The voltage of the capacitive element Cb is set to a voltage corresponding to the electric charge stored in the capacitor (capacitive element Ca) of the partial detection area PAA at a location where the third switching element TrS is turned on in response to the selection signal ASW(k). After the output voltage ($V_{out}$) of the third switching element TrS is set to the reference potential (Vref) due to the imaginary short-circuit, the output voltage of the detection signal amplifier 42 reaches a voltage corresponding to the capacitance of the capacitive element Cb, and this output voltage is read by the A/D converter 43. The voltage of the capacitive element Cb is, for example, a voltage between two electrodes provided on a capacitor constituting the capacitive element Cb.

The period t1 is 20 μs, for example. The period t2 is 60 μs, for example. The period t3 is 44.7 μs, for example. The period t4 is 0.98 μs, for example.

Although FIGS. 7 and 8 illustrate the example in which the gate line drive circuit 15 individually selects the gate line GCL, the present disclosure is not limited to this example. The gate line drive circuit 15 may simultaneously select a predetermined number (two or more) of the gate lines GCL and sequentially supply the gate drive signals Vgcl to the gate lines GCL in units of the predetermined number of the gate lines GCL. The signal line selection circuit 16 may also simultaneously electrically couple a predetermined number (two or more) of the signal lines SGL to one detection circuit 48. Moreover, the gate line drive circuit 15 may scan some of the gate lines GCL while skipping the others.

Figure 9:
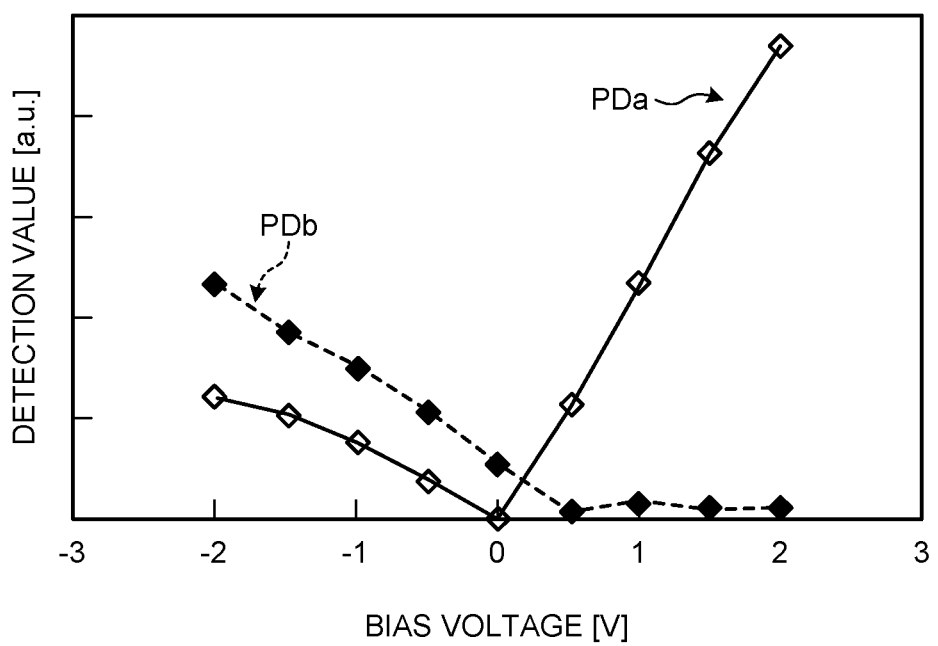
FIG. 9 is a graph schematically illustrating relations between a bias voltage and a detection value.

The following describes a relation of the bias voltage VB with characteristics of the optical sensor PD. FIG. 9 is a graph schematically illustrating relations between the bias voltage and the detection value. FIG. 9 illustrates the relation of the bias voltage VB with the detection value for each of the first and the second photodiodes PDa and PDb of the optical sensor PD. The horizontal axis of the graph illustrated in FIG. 9 represents the bias voltage VB supplied to the optical sensor PD, and the vertical axis represents the detection value from the optical sensor PD. The detection value is a voltage signal output from the detection circuit 48. Alternatively, the detection value may be the output voltage ($V_{out}$) of the third switching element TrS illustrated in FIG. 4.

With reference to FIG. 9, a case will be described where the first photodiode PDa detects the visible light (with a wavelength of from 400 nm to 650 nm, for example, 525 nm), and the second photodiode PDb detects the near-infrared light (with a wavelength of from 780 nm to 950 nm, for example, 850 nm).

As illustrated in FIG. 9, when the bias voltage VB has a negative polarity, the first photodiode PDa is driven in the forward biased state, and the second photodiode PDb is driven in the reverse biased state. As a result, the current flowing through the second photodiode PDb is detected. Therefore, when the bias voltage VB has the negative polarity, the optical sensor PD is mainly sensitive to the near-infrared light. The second photodiode PDb is sensitive to the visible light in addition to the near-infrared light. Therefore, as illustrated in FIG. 9, the optical sensor PD is sensitive to the near-infrared light and the visible light when the bias voltage VB has the negative polarity.

When the bias voltage VB has a positive polarity, the first photodiode PDa is driven in the reverse biased state and the second photodiode PDb is driven in the forward biased state. As a result, the current flowing through the first photodiode PDa is detected. Therefore, when the bias voltage VB has the positive polarity, the optical sensor PD is mainly sensitive to the visible light.

Thus, the detection device 1 can change the wavelength range of the light L1 to which the optical sensor PD is sensitive by switching the polarity of the bias voltage VB. In other words, compared with a case where the optical sensor PD is formed of either the first photodiode PDa or the second photodiode PDb, the detection device 1 can be sensitive to different wavelength ranges, and thus can acquire different items of biometric information, such as the fingerprint with sensitivity in the visible range and the vascular pattern with sensitivity in the infrared range, using the optical sensor allowed to have sensitivity to different wavelength ranges by changing the direction of the application voltage and the light sources of one type configured to emit light having light emission wavelengths corresponding to the different wavelength ranges allowed to be detected with different detection sensitivity. Since the sensitivity can be set for two different wavelengths, the measurements of the blood oxygen saturation level that require information at different wavelengths can be acquired using the optical sensor allowed to have sensitivity to different wavelength ranges by changing the direction of the application voltage and the light sources of one type configured to emit light having light emission wavelengths corresponding to the different wavelength ranges allowed to be detected with different detection sensitivity. While the case has been described where the first photodiode PDa is sensitive in the visible range and the second photodiode PDb is sensitive in the infrared range, the wavelength ranges of the sensitivity are not limited to this case. The present disclosure also includes a case where the first photodiode PDa and the second photodiode PDb are sensitive in different ranges of the visible range, a case where the first photodiode PDa and the second photodiode PDb are sensitive in different ranges of the infrared range, and a case where the first photodiode PDa or the second photodiode PDb is or both of them are sensitive in a wavelength range of ultraviolet rays. The first and the second photodiodes PDa and PDb are not limited to being applied to biometric sensors, but can also be applied to, for example, color scanners or color image detection devices. In this case, to detect a color image, only two pixels are required instead of three pixels having different sensitivity to red, green, and blue (RGB). That is, one of the two pixels is sensitive to two wavelength ranges, and the other pixel is sensitive to one or two wavelength ranges. Thus, the two pixels may be set to be sensitive to three or four wavelength ranges.

Figure 10:
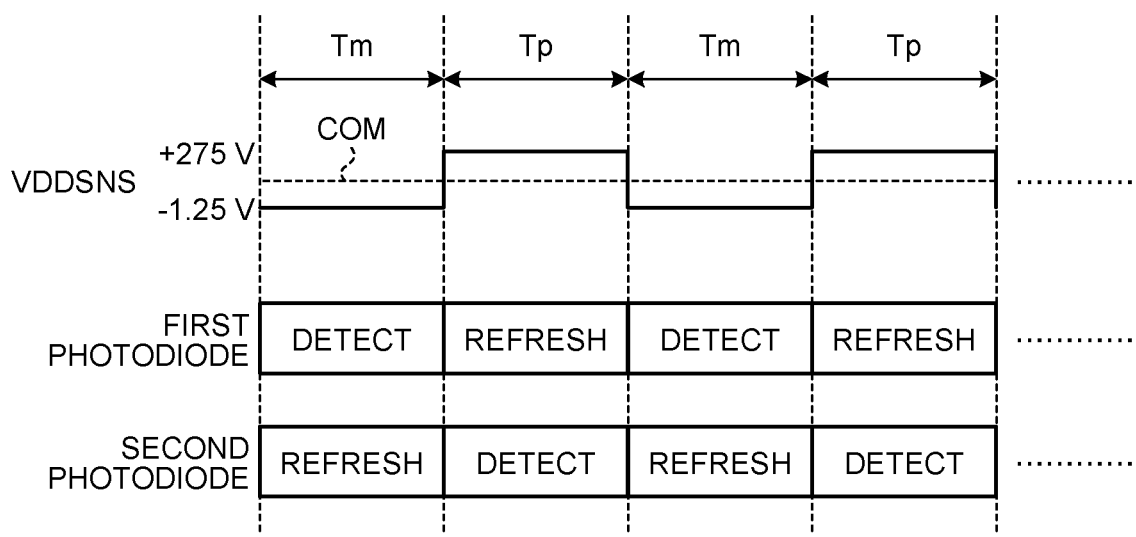
FIG. 10 is an explanatory diagram for explaining an exemplary method for driving the detection device.

FIG. 10 is an explanatory diagram for explaining an exemplary method for driving the detection device. As illustrated in FIG. 10, in the detection device 1, a period Tm and a period Tp is alternately provided in a time-division manner. The period Tm is a period in which the drive signal VDDSNS having the negative polarity (for example, VDDSNS=−1.25 V) is supplied to the optical sensor PD, and the period Tp is a period in which the drive signal VDDSNS having the positive polarity (for example, VDDSNS=+2.75 V) is supplied to the optical sensor PD. In other words, the period Tm is a period in which the drive signal supply circuit 123a (refer to FIG. 4) operates the switch BSW to supply the second voltage signal VL to the second terminal N2 of the light sensor PD. The period Tp is a period in which the drive signal supply circuit 123a (refer to FIG. 4) operates the switch BSW to supply the first voltage signal VH to the second terminal N2 of the light sensor PD. Thus, the drive signal supply circuit 123a supplies the first voltage signal VH and the second voltage signal VL to the light sensor PD in a time-division manner so as to alternately invert the polarity of the bias voltage VB for each of the periods Tm and Tp.

The first photodiode PDa is refreshed in the period Tp and performs the detection in the period Tm. The second photodiode PDb performs the detection in the period Tp and is refreshed in the period Tm. The period of performing the detection and the period of performing the refreshing are alternately arranged for the first and the second photodiodes PDa and PDb. Therefore, the optical sensor PD can reduce time-dependent changes in detection sensitivity.

During the period in which one of the first and the second photodiodes PDa and PDb is performing the detection, the other of the first and the second photodiodes PDa and PDb is refreshed. Therefore, the optical sensor PD can restrain the detection speed from decreasing, compared with a case where the optical sensor PD is formed of one photodiode, and the period for detection and the period for refreshing are individually provided.

The periods Tm and Tp may be arranged in any way. For example, the periods Tm and Tp may alternate every one detection frame period in which the gate line drive circuit 15 scans all the gate lines GCL (gate lines GCL(1) to GCL(M)). Alternatively, the periods Tm and Tp may be provided in one detection frame period. Alternatively, the periods Tm and Tp may alternate every multiple detection frames.

When the first and the second photodiodes PDa and PDb detect the light having different wavelengths, for example, when the first photodiode PDa detects the visible light and the second photodiode PDb detects the near-infrared light as described above, the first and the second light sources 61 and 62 (refer to FIG. 1) that emit the light may be switched on and off for each of the periods Tm and Tp.

The configuration is not limited to the case where the first photodiode PDa detects the visible light and the second photodiode PDb detects the near-infrared light, but may be such that the first photodiode PDa detects the near-infrared light and the second photodiode PDb detects the visible light. Alternatively, the first and the second photodiodes PDa and PDb may be configured to detect light in the same wavelength range.

As described above, the detection device 1 of the present embodiment is the detection device 1 including the optical sensors PD arranged on a substrate (sensor base member 21), and the optical sensors PD each include the first photodiode PDa and the second photodiode PDb that is coupled in series and in the opposite direction to the first photodiode PDa.

With this configuration, when the bias voltage VB is supplied to the optical sensor PD, one of the first and the second photodiodes PDa and PDb is driven in the reverse biased state to perform the detection, and the other of the first and the second photodiodes PDa and PDb is driven in the forward biased state to be refreshed. Therefore, compared with the case where the optical sensor PD is formed of one photodiode, and the detection period and the refreshing period are executed in a time-division manner, the detection device 1 can reduce time-dependent changes in sensitivity characteristics while restraining the detection speed from decreasing.

Figure 11:
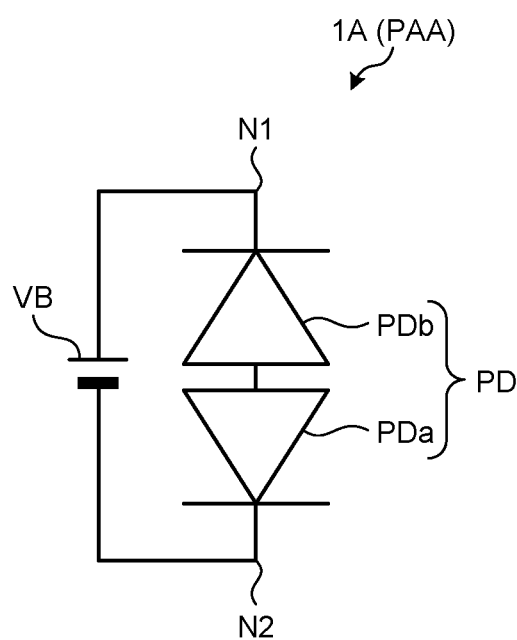
FIG. 11 is a circuit diagram illustrating a portion of one of the partial detection areas according to a modification.

FIG. 11 is a circuit diagram illustrating a portion of the partial detection area according to a modification. As illustrated in FIG. 11, a detection device 1A of the modification has a different coupling configuration between the first and the second photodiodes PDa and PDb from that of the first embodiment described above. Specifically, the cathode of the second photodiode PDb is electrically coupled to the first terminal N1; the anode of the first photodiode PDa is electrically coupled to the anode of the second photodiode PDb; and the cathode of the first photodiode PDa is electrically coupled to the second terminal N2.

Figure 12:
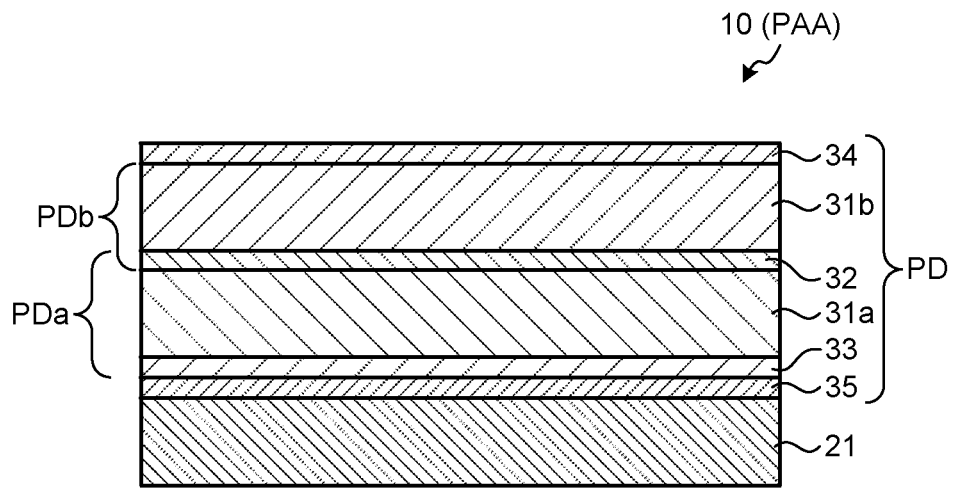
FIG. 12 is a sectional view illustrating a schematic sectional configuration of the optical sensor according to the modification.

FIG. 12 is a sectional view illustrating a schematic sectional configuration of the optical sensor according to the modification. As illustrated in FIG. 12, the sensor 10 according to the modification includes the sensor base member 21 and the optical sensor PD. The sensor base member 21 is a glass substrate. The optical sensor PD is provided above the sensor base member 21. The optical sensor PD is stacked on the sensor base member 21 in the order of the first photodiode PDa and the second photodiode PDb. More specifically, the optical sensor PD is stacked on the sensor base member 21 in the order of the lower electrode 35 (first electrode), the electron transport layer 33, the first active layer 31a, the hole transport layer 32, the second active layer 31b, and the upper electrode 34 (second electrode).

The lower electrode 35 is formed of, for example, a light-transmitting conductive material such as ITO. Zinc oxide (ZnO) is used as a material of the electron transport layer 33.

The first active layer 31a is formed of poly(3-hexylthiophene) (P3HT):(6,6)-phenyl-$C_{61}$-butyric acid methyl ester (PCBM). P3HT is a p-type semiconductor; PCBM is an n-type semiconductor; and P3HT:PCBM is an organic photodiode (OPD) having a heterojunction structure of a mixture of P3HT and PCBM.

A polythiophene-based conductive polymer (poly(3,4-ethylenedioxythiophene) (PEDOT)):poly(styrene sulfonate) (PSS) is used as the hole transport layer 32.

The second active layer 31b is formed of poly((2,5-bis (2-hexyldecyl)-2,3,5,6-tetrahydro-3,6-dioxopyrrolo(3,4-c) pyrrole-1,4-diyl)-alt-(3',3"-dimethyl-2,2': 5',2"-terthiophene)-5,5"-diyl) (PMDPP3T):(6,6)-Phenyl $C_{61}$ butyric acid methyl ester (PCBM). PMDPP3T is a p-type semiconductor; PCBM is an n-type semiconductor; and PMDPP3T:PCBM is an organic photodiode (OPD) having a heterojunction structure of a mixture of PMDPP3T and PCBM.

For example, aluminum (Al) is used as the upper electrode 34.

Figure 13:
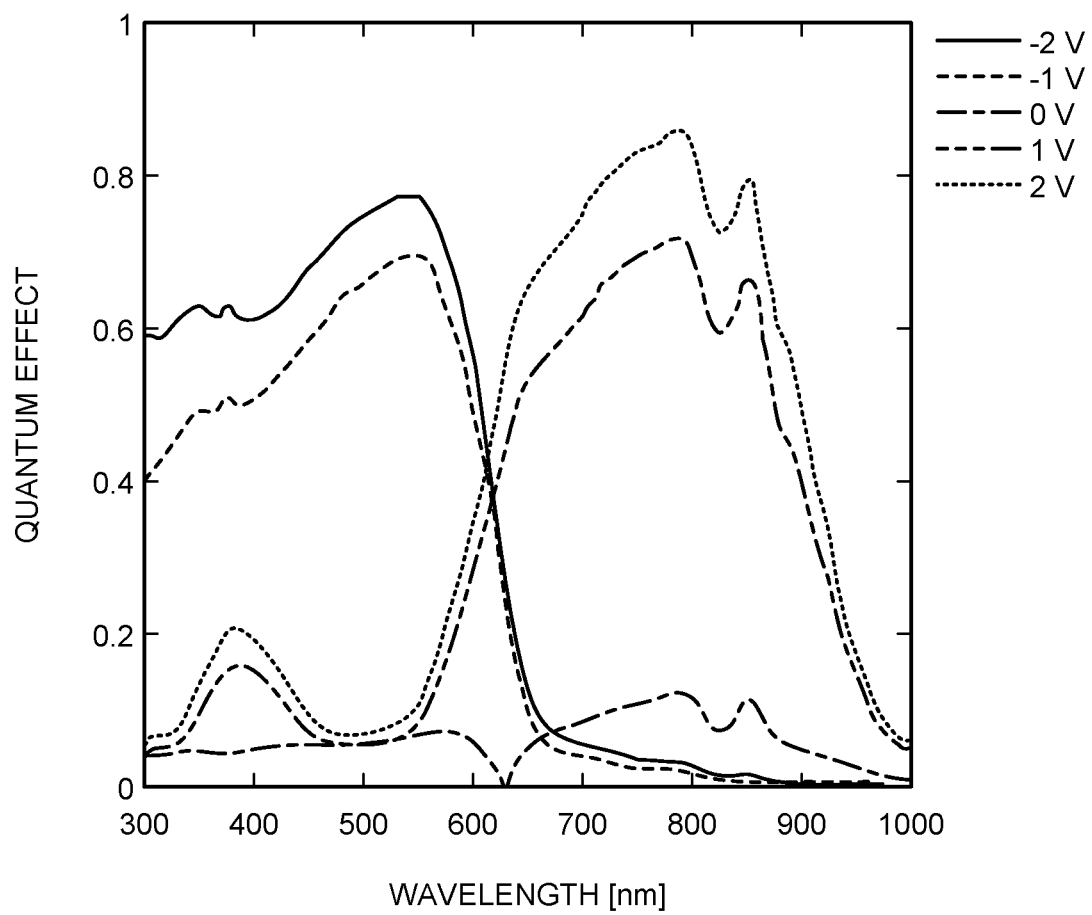
FIG. 13 is a graph schematically illustrating wavelength sensitivity characteristics of the optical sensor according to the modification.

FIG. 13 is a graph schematically illustrating wavelength sensitivity characteristics of the optical sensor according to the modification. As illustrated in FIG. 13, when the bias voltage VB has the negative polarity, the first photodiode PDa is driven in the reverse biased state and the second photodiode PDb is driven in the forward biased state. As a result, the current flowing through the first photodiode PDa is detected. Therefore, when the bias voltage VB has the negative polarity, the optical sensor PD is mainly sensitive to the visible light.

When the bias voltage VB has the positive polarity, the second photodiode PDb is driven in the reverse biased state, and the first photodiode PDa is driven in the forward biased state. As a result, the current flowing through the second photodiode PDb is detected. Therefore, when the bias voltage VB has the positive polarity, the optical sensor PD is mainly sensitive to the near-infrared light.

Second Embodiment

Figure 14:
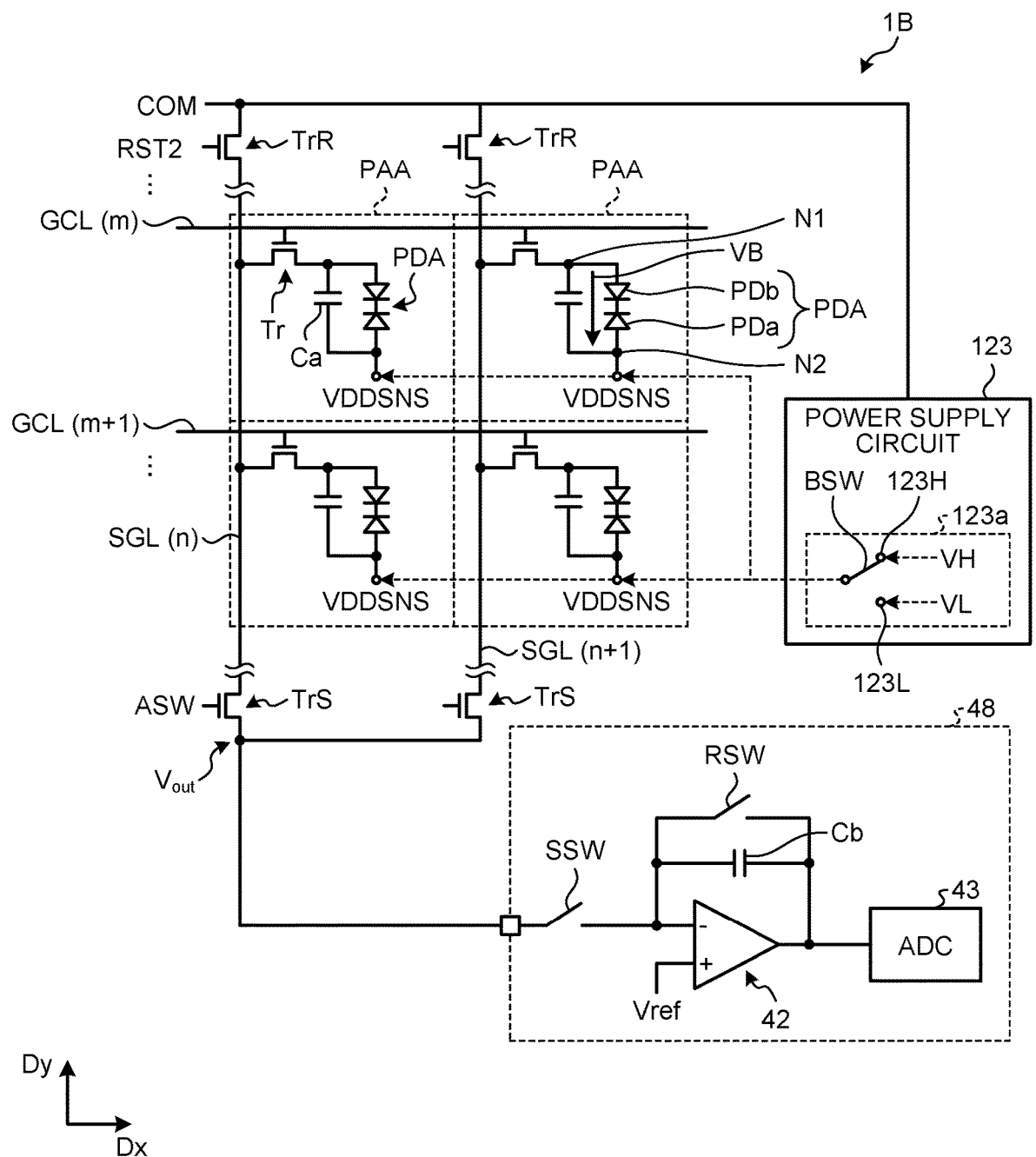
FIG. 14 is a circuit diagram illustrating a detection device according to a second embodiment.

FIG. 14 is a circuit diagram illustrating a detection device according to a second embodiment. In the following description, the same components as those described in the embodiment described above are denoted by the same reference numerals, and the description thereof will not be repeated.

As illustrated in FIG. 14, a detection device 1B of the second embodiment has a different coupling configuration of an optical sensor PDA from that of the optical sensor PD of the first embodiment described above. Specifically, the anode of the first photodiode PDa is electrically coupled to the second terminal N2; the cathode of the first photodiode PDa is electrically coupled to the cathode of the second photodiode PDb; and the anode of the second photodiode PDb is electrically coupled to the first terminal N1. Also in the second embodiment, the first and the second photodiodes PDa and PDb are coupled in series and in opposite directions between the first terminal N1 on the one end side and the second terminal N2 on the other end side of the optical sensor PDA.

In the second embodiment, the rectification characteristics of each of the first and the second photodiodes PDa and PDb are inverted with respect to the configuration of the first embodiment. Therefore, when the bias voltage VB of −2.0 V is supplied to the optical sensor PDA (for example, in the period Tm in FIG. 10), the first photodiode PDa is driven in the forward biased state (refreshed), and the second photodiode PDb is driven in the reverse biased state (performs detection). When the bias voltage VB of +2.0 V is supplied to the optical sensor PDA (for example, in the period Tp in FIG. 10), the first photodiode PDa is driven in the reverse biased state (performs detection) and the second photodiode PDb is driven in the forward biased state (refreshed).

While the preferred embodiments of the present disclosure have been described above, the present disclosure is not limited to the embodiments described above. The content disclosed in the embodiments is merely an example, and can be variously modified within the scope not departing from the gist of the present disclosure. Any modifications appropriately made within the scope not departing from the gist of the present disclosure also naturally belong to the technical scope of the present disclosure. At least one of various omissions, substitutions, and changes of the components can be made without departing from the gist of the embodiments and the modification described above.

What is claimed is:
1. A detection device comprising
a plurality of optical sensors arranged on a substrate in first and second directions along a plane of the substrate which has a normal direction orthogonal to the plane of the substrate, wherein
each of the optical sensors comprises:
a first photodiode; and
a second photodiode that is coupled in series and in an opposite direction to the first photodiode, wherein
the first photodiode is stacked on the second photodiode in the normal direction,
the optical sensors are configured such that a first electrode, an electron transport layer, a first active layer, a hole transport layer, a second active layer, and a second electrode are stacked in the normal direction of the substrate in the order as listed, the first active layer includes a p-n heterojunction of the first photodiode, the second active layer includes a p-n heterojunction of the second photodiode, the first active layer is in direct contact with the hole transport layer, and the second active layer is in direct contact with the hole transport layer.

2. The detection device according to claim 1, wherein the first photodiode and the second photodiode have different sensitivity characteristics from each other with respect to a wavelength of light.

3. The detection device according to claim 1, wherein the first photodiode is configured to detect visible light, and the second photodiode is configured to detect near-infrared light.

4. The detection device according to claim 1, further comprising a drive signal supply circuit configured to supply a drive signal to the optical sensors, wherein the drive signal supply circuit is configured to supply a first voltage signal having a higher-level voltage than that of a reference potential and a second voltage signal having a lower-level voltage than that of the reference potential to the optical sensors in a time-division manner.

5. The detection device according to claim 1, wherein the second photodiode is configured to perform detection when the first photodiode is driven in a forward biased state and the second photodiode is driven in a reverse biased state, and the first photodiode is configured to perform detection when the first photodiode is driven in the reverse biased state and the second photodiode is driven in the forward biased state.

6. The detection device according to claim 1, wherein the optical sensors correspond to a plurality partial detection areas arranged in a matrix having a row-column configuration, the first photodiodes of the optical sensors are disposed on a different plane from a plane on which the second photodiodes of the optical sensors are disposed, and the first photodiodes are non-uniform and the second photodiodes are non-uniform such that a current flowing through the optical sensor during an exposure period varies for each of the partial detection areas.

7. The detection device according to claim 1, wherein no electron transport layer is formed between the first active layer and the second active layer.

* * * * *